US00PP18853P2

(12) United States Plant Patent
Uchneat

(10) Patent No.: US PP18,853 P2
(45) Date of Patent: May 27, 2008

(54) ***IMPATIENS* PLANT NAMED 'BALFIESALMO'**

(50) Latin Name: *Impatiens walleriana*
Varietal Denomination: Balfiesalmo

(75) Inventor: Michael S. Uchneat, Geneva, IL (US)

(73) Assignee: Ball Horticultural Company, West Chicago, IL (US)

( * ) Notice: Subject to any disclaimer, the term of this patent is extended or adjusted under 35 U.S.C. 154(b) by 67 days.

(21) Appl. No.: 11/602,817

(22) Filed: Nov. 21, 2006

(51) Int. Cl.
*A01H 5/00* (2006.01)

(52) U.S. Cl. ..... Plt./319

(58) Field of Classification Search ..... Plt./319
See application file for complete search history.

*Primary Examiner*—Annette H Para
(74) *Attorney, Agent, or Firm*—Audrey Charles

(57) ABSTRACT

A new and distinct cultivar of *Impatiens* plant named 'Balfiesalmo', characterized by its double type, medium salmon-colored flowers, dark green-colored foliage, and vigorous, compact, and upright-mounded growth habit.

1 Drawing Sheet

Latin name of genus and species of plant claimed: *Impatiens walleriana.*
Variety denomination: 'Balfiesalmo'.

BACKGROUND OF THE INVENTION

The present invention relates to a new and distinct cultivar of *Impatiens* plant botanically known as *Impatiens walleriana* and hereinafter referred to by the cultivar name 'Balfiesalmo'.

The new cultivar originated in a controlled breeding program in Elbum, Ill. during February 2000. The objective of the breeding program was the development of *Impatiens* cultivars with fully double-type flowers, attractive flower and foliage coloration, and a freely branching, compact growth habit.

The new *Impatiens* cultivar is the result of cross-pollination. The female (seed) parent of the new cultivar is the proprietary *Impatiens walleriana* breeding selection designated SDC1712, not patented, characterized by its semi-double type, coral-colored flowers, dark, olive-green-colored foliage, and mounded, well branched growth habit. The male (pollen) parent of the new cultivar is the proprietary *Impatiens walleriana* breeding selection designated 12865-2, not patented, characterized by its double type, medium cherry-colored flowers, medium green-colored foliage, and upright-mounded growth habit. The new cultivar was discovered and selected as a single flowering plant within the progeny of the above stated cross-pollination during August 2000 in a controlled environment at Elbum, Ill.

Asexual reproduction of the new cultivar by terminal stem cuttings since August 2000 at Arroyo Grande, Calif., and West Chicago, Ill, has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balfiesalmo' as a new and distinct cultivar of *Impatiens* plant:

1. Double type, medium salmon-colored flowers;
2. Dark green-colored foliage; and
3. Vigorous, compact, and upright-mounded growth habit.

Plants of the new cultivar differ from plants of the female parent primarily in flower type and flower color and from plants of the male parent primarily in flower color, flower size, and foliage color.

Of the many commercially available *Impatiens* cultivars known to the inventor, the most similar in comparison to the new cultivar is Fiesta™ 'Salmon Sunrise', U.S. Plant Pat. No. 9,691. However, in side by side comparisons, plants of the new cultivar differ from plants of 'Salmon Sunrise' in the following characteristics:

1. Plants of the new cultivar are shorter than plants of 'Salmon Sunrise';
2. Plants of the new cultivar are wider than plants of 'Salmon Sunrise'; and
3. Plants of the new cultivar have larger flowers than plants of 'Salmon Sunrise'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balfiesalmo'. The plants were grown in 4.5 inch pots for 12 weeks in a greenhouse at West Chicago, Ill.

DETAILED BOTANICAL DESCRIPTION

Figure 1:
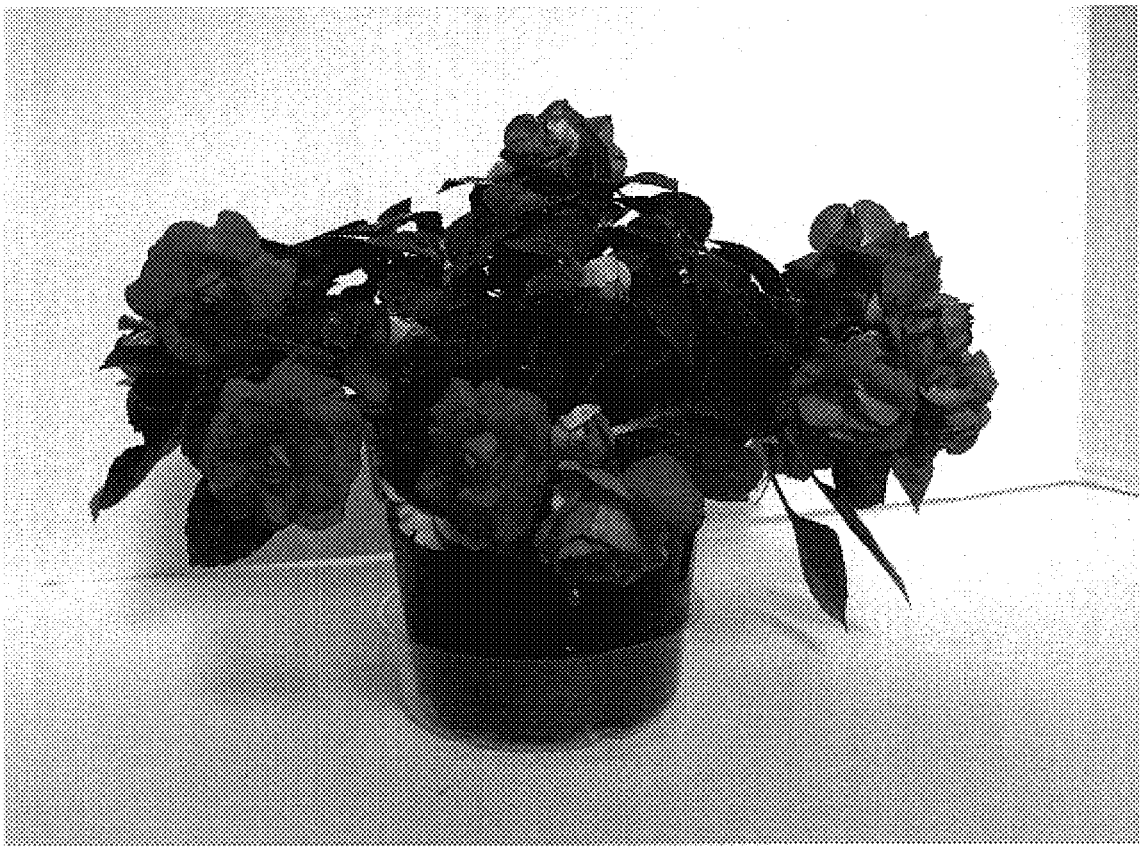
FIG. 1 illustrates a side view of the overall growth and flowering habit of 'Balfiesalmo'.
Figure 2:
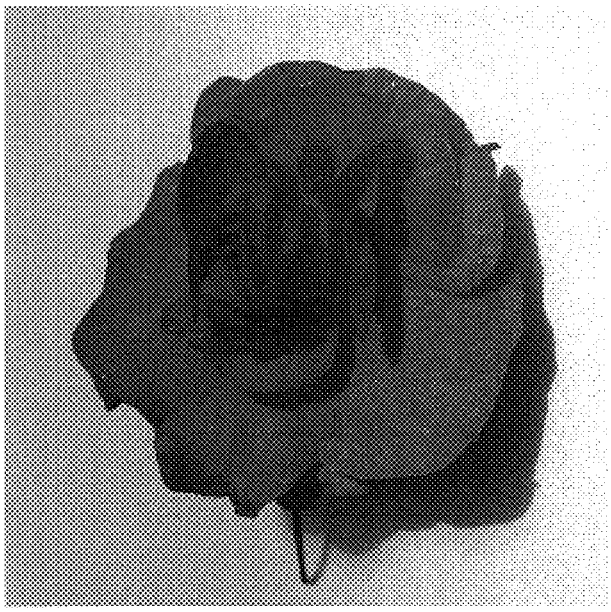
FIG. 2 illustrates a close-up view of an individual flower of 'Balfiesalmo'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Feb. 21, 2006 between 9:00 a.m. and 11:00 a.m. under natural light conditions in West Chicago, Ill.

The following descriptions and measurements describe plants produced from cuttings taken from stock plants and grown in a glass-covered greenhouse under conditions comparable to those used in commercial practice. The plants were grown at West Chicago, Ill. in 4.5 inch pots for 12 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Impatiens walleriana* cultivar Balfiesalmo.

Parentage:

*Female parent.*—Proprietary *Impatiens walleriana* breeding selection designated SDC1712, not patented.

*Male parent.*—Proprietary *Impatiens walleriana* breeding selection designated 12865-2, not patented.

Propagation:

*Type cutting.*—Terminal stem.

*Time to initiate roots.*—Approximately 7 to 8 days.

*Time to produce a rooted cutting.*—Approximately 21 to 24 days.

*Root description.*—Fibrous.

*Rooting habit.*—Freely branching.

Plant description:

*Commercial crop time.*—Approximately 6 to 9 weeks from a rooted cutting.

*Growth habit and general appearance.*—Vigorous, compact, and upright-mounded.

*Size*—Height from soil level to top of plant plane: Approximately 9.1 cm. Width: Approximately 28.9 cm.

*Branching habit.*—Freely basal branching. Quantity of main branches per plant: Approximately 7.

*Branch.*—Strength: Moderately strong. Length: Approximately 9.5 cm. Diameter: Approximately 3.3 mm. Length of central internode: Approximately 1.9 cm. Texture: Glabrous. Color of young and mature stems: 143C with streaks of 187C at node regions.

Foliage description:

*General description.*—Quantity of leaves per main branch: Approximately 10. Fragrance: none. Form: Simple. Arrangement: Alternate.

*Leaves.*—Aspect: Acute angle to stem. Shape: Ovate. Margin: Crenate, ciliate. Apex: Acute. Base: Attenuate. Venation pattern; Pinnate. Length of mature leaf at center of stem: Approximately 5.0 cm. Width of mature leaf at center of stem: Approximately 3.3 cm. Texture of upper and lower surfaces: Glabrous. Color of upper surface of young foliage: 137A with splotches of N186C and venation of 138C. Color of lower surface of young foliage: 191B with strong splotches of N186C and venation of 138C. Color of upper surface of mature foliage: 137A with very faint splotches of N186C and venation of 138C. Color of lower surface of mature foliage: 191B with faint splotches of N186C and venation of 138C.

*Petiole.*—Length: Approximately 2.0 cm. Diameter: Approximately 2.1 mm. Texture: Glabrous. Color: 138B.

Flowering description:

*Flowering habit.*—'Balfiesalmo' is freely flowering under outdoor growing conditions with substantially continuous blooming from spring through autumn and year-round in greenhouse environment.

*Lastingness of individual flower on the plant.*—Approximately 6 to 9 days.

Flower description:

*General description.*—Type: Double. Quantity per plant: Approximately 14. Fragrance: None.

*Bud.*—Rate of opening: Generally takes 3 to 5 days for bud to progress from first color to fully open flower. Quantity showing color per plant: Approximately 2.9.

*Bud just before opening.*—Shape: Oval. Length: Approximately 1.3 cm. Diameter: Approximately 1.0 cm. Color: 51B.

*Corolla.*—Shape: Hemispherical. Width: Approximately 4.4 cm. Depth: Approximately 2.6 cm. Borne: Above the foliage.

*Petals.*—Quantity: 32. Shape: Obovate. Aspect: Flat. Appearance: Iridescent. Margin: Entire. Apex: Obtuse, some are emarginate. Base: Attenuate. Length of outermost petal: Approximately 2.1 cm. Width of outermost petal: Approximately 1.7 cm. Length of innermost petals: Approximately 7.3 mm. Width of innermost petals: Approximately 5.3 mm. Texture of upper and lower surfaces: Glabrous. Colors of upper surface when first open: 41A. Color of lower surface when first open: 41D. Color of upper surface when fully open: 41A fading to 41C with age. Color of lower surface when fully open: 41D.

*Spur.*—Quantity: 1 per flower. Length: Approximately 3.8 cm. Diameter at tip: Less than 1 mm. Diameter at base: Approximately 2.0 mm. Texture: Glabrous. Color: 160C at base transitioning to 187B at tip.

*Peduncle.*—Strength: Moderately strong. Aspect: Acute angle to stem. Length: Approximately 2.8 cm. Diameter: Approximately 2.0 mm. Texture: Glabrous. Color: 144B.

*Sepals.*—Quantity per flower: 4, with one fused to base of upper petal. Shape of lateral sepals: Lanceolate. Shape of lower sepal: Trifid. Apex of all sepals: Acute. Length of lateral sepals: Approximately 2.0 mm. Width of lateral sepals: Approximately 1.0 mm. Length of lower sepal: Approximately 6.0 mm. Width of lower sepal: Approximately 1.2 cm. Texture of upper and lower surfaces of all sepals: Glabrous. Color of lateral sepals: 144B with 187B at apex. Color of lower sepal: Closest to 158D with a central spot of N186B.

*Reproductive organs.*—None observed.

Seed and fruit production: Neither seed not fruit production has been observed.

Disease and pest resistance: Resistance to pathogens and pests common to *Impatiens* has not been observed.

What is claimed is:

1. A new and distinct cultivar of *Impatiens* plant named 'Balfiesalmo', substantially as herein shown and described.

* * * * *